US010952888B2

(12) United States Patent
Popovic et al.

(10) Patent No.: US 10,952,888 B2
(45) Date of Patent: *Mar. 23, 2021

(54) VARIABLE STIFFNESS DEVICES AND METHODS OF USE

(71) Applicant: Worcester Polytechnic Institute, Worcester, MA (US)

(72) Inventors: Marko Popovic, Worcester, MA (US); Saivimal Sridar, Worcester, MA (US); Corey Majeika, Worcester, MA (US); Nicholas Deisadze, Worcester, MA (US); Erika Giancarlo, Worcester, MA (US)

(73) Assignee: Worcester Polytechnic Institute, Worcester, MA (US)

( * ) Notice: Subject to any disclaimer, the term of this patent is extended or adjusted under 35 U.S.C. 154(b) by 440 days.

This patent is subject to a terminal disclaimer.

(21) Appl. No.: 16/014,386

(22) Filed: Jun. 21, 2018

(65) Prior Publication Data
US 2018/0296382 A1    Oct. 18, 2018

Related U.S. Application Data

(63) Continuation of application No. 15/154,443, filed on May 13, 2016, now Pat. No. 10,028,855.
(Continued)

(51) Int. Cl.
*A61F 5/05* (2006.01)
*A61F 5/058* (2006.01)
(Continued)

(52) U.S. Cl.
CPC ............. *A61F 5/058* (2013.01); *A61F 2/50* (2013.01); *A61F 5/01* (2013.01); *B25J 19/068* (2013.01);
(Continued)

(58) Field of Classification Search
CPC .. A61F 5/058; A61F 5/05808; A61F 5/05816; A61F 5/05833; A61F 5/05;
(Continued)

(56) References Cited

U.S. PATENT DOCUMENTS 3,638,536 A * 2/1972 Kleinwachter ....... F15B 15/103
92/92
5,083,498 A     1/1992 Sato et al.
(Continued)

FOREIGN PATENT DOCUMENTS

WO      2013184192 A2    12/2013

OTHER PUBLICATIONS

International Search Report in International Patent Application No. PCT/US2016/032458 dated Feb. 2, 2017.

*Primary Examiner* — Tarla R Patel
(74) *Attorney, Agent, or Firm* — Greenberg Traurig, LLP; Roman Fayerberg; Jaime Burke

(57) ABSTRACT

Variable stiffness devices and methods of their use are provided. In some embodiments, a variable stiffness device comprises an inner member defining a compartment for receiving an actuating fluid; an outer member disposed around the inner member; and a granular medium disposed between the inner member and the outer member; wherein the inner member is being moveable in a radial direction from a relaxed state to an expanded state by introducing the actuating fluid into the compartment of the inner member to compress the granular medium against the outer member to increase the stiffness of the device.

19 Claims, 9 Drawing Sheets

Related U.S. Application Data

(60) Provisional application No. 62/161,865, filed on May 14, 2015.

(51) Int. Cl.
    *A61F 5/01* (2006.01)
    *A61F 2/50* (2006.01)
    *B25J 19/06* (2006.01)
    *A61F 2/74* (2006.01)

(52) U.S. Cl.
    CPC . *A61F 2002/503* (2013.01); *A61F 2002/5066* (2013.01); *A61F 2002/745* (2013.01); *A61F 2005/0155* (2013.01); *A61F 2005/0169* (2013.01)

(58) Field of Classification Search
    CPC .. A61F 5/0102; B25J 9/142; B25J 9/14; B25J 9/144; B25J 9/146
    USPC .......................................................... 623/26
    See application file for complete search history.

(56) References Cited

U.S. PATENT DOCUMENTS

| | | | |
|---|---|---|---|
| 7,213,503 B2 | 5/2007 | Asai et al. | |
| 7,413,554 B2 | 8/2008 | Kobayashi et al. | |
| 10,028,855 B2 * | 7/2018 | Popovic | A61F 2/50 |
| 2016/0331572 A1 | 11/2016 | Popovic et al. | |

* cited by examiner

VARIABLE STIFFNESS DEVICES AND METHODS OF USE

RELATED APPLICATIONS

This application is a continuation patent application of U.S. patent application Ser. No. 15/154,443, filed May 13, 2016, which claims the benefit of and priority to U.S. Provisional Patent Application No. 62/161,865, filed on May 14, 2015, each of which are incorporated herein by reference in their entireties.

FIELD

The present disclosure relates to variable stiffness devices with variable stiffness and shape, and methods of their use.

BACKGROUND

There are many potential uses for devices with variable stiffness and shape, such as active suspensions in automobiles, wearable devices, and civil engineering structures. For example, in stroke patients, loss of muscle function is common and causes significant weakness in the lower leg. In severe cases there may be complete paralysis of the legs. Therefore, in case of post-stroke and injury rehabilitation, it may be required that the load on such type of weak bones and muscles is kept to a minimum. Variable stiffness devices can be used to provide motion assistance to stroke patients, with the stiffness being varied as necessary to strengthen their muscles and bones. Accordingly, there is a need for devices that can provide a range of stiffness, while being easy to use.

SUMMARY

Fluid operated devices with variable stiffness and shape and methods of use are provided. A device may comprise one or more inner members made from an elastic material and defining a compartment for receiving an actuating fluid, the inner members being moveable in a radial, longitudinal direction or both from a relaxed state to an expanded state by introducing an actuating fluid into the inner members; and an outer member made from an inelastic material and being disposed around the inner members to control expansion of the inner member in a radial or longitudinal direction, and a granular material disposed between the outer and inner members, which is compressed by the inner members against the outer member to increase the stiffness of the device.

In some embodiments, a variable stiffness device comprises an inner member defining a compartment for receiving an actuating fluid; an outer member disposed around the inner member; and a granular medium disposed between the inner member and the outer member; wherein the inner member is being moveable in a radial direction from a relaxed state to an expanded state by introducing the actuating fluid into the compartment of the inner member to compress the granular medium against the outer member to increase the stiffness of the device.

In some embodiments, the inner member is made from an elastic material and the outer member is made from a non-stretchable material. In some embodiments, the outer member has a fixed size in the radial direction and a variable size in a longitudinal direction. In some embodiments, the outer member is reinforced on a side to direct bending of the outer member under a load. In some embodiments, the outer member is pre-bent to a side to direct bending of the outer member under a load. In some embodiments, the granular medium is compressible. In some embodiments, the granular medium is a mixture of rubber pellet granules ranging from about 1 to about 3 mm in diameter. In some embodiments, the granular medium has a packing factor between about 0.55 and about 0.74 at atmospheric pressure. In some embodiments, the variable stiffness device is incorporated into an article of clothing.

In some embodiments, a variable stiffness device comprises a first inner members, the first inner member defining a first compartment for receiving a first actuating fluid; a second inner member wrapped around the first inner member, the second inner member defining a second compartment for receiving a second actuating fluid; an outer member disposed around the inner member; and a granular medium disposed between the second inner member and the outer member; wherein the first inner member is configured to expand in a longitudinal direction by introducing the first actuating fluid into the first compartment of the first inner member to expand the variable stiffness device in the longitudinal direction; and wherein the second inner member is configured to expand in a radial direction by introducing the second actuating fluid into the second compartment of the second inner member to compress the granular medium against the outer member to increase the stiffness of the variable stiffness device.

In some embodiments, a method for providing structural support to a structure comprises disposing a variable stiffness device in connection with a structure in need of structural support, the variable stiffness device comprising an inner member defining a compartment for receiving an actuating fluid; an outer member disposed around the inner member; and a granular medium disposed between the inner member and the outer member; expanding the inner member by introducing the actuating fluid into the compartment of the inner member to compress the granular medium against the outer member; and adjusting the amount of the actuating fluid in the compartment to vary an amount of structural support provided by the variable stiffness device.

DESCRIPTION OF THE DRAWINGS

The presently disclosed embodiments will be further explained with reference to the attached drawings. The drawings shown are not necessarily to scale, with emphasis instead generally being placed upon illustrating the principles of the presently disclosed embodiments.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The present disclosure provides a variable stiffness device that has variable stiffness and can be used to mimic the overall performance of bone. According to some aspects of the present disclosure, there is provided a fluid operated (hydraulic and pneumatic) device comprising an inner member made from an elastic material and defining a compartment for receiving an actuating fluid, an outer member made from an inelastic, non-stretchable material and being disposed around the elastic inner member, and a granular medium disposed between the inner member and the outer member. The devices of the present disclosure may be pressurized either with liquid (hydraulically) or with gas (pneumatically). The outer member may have a fixed maximum length so it cannot be extended or stretched beyond such maximum length. The inner member can be moveable in a radial direction, longitudinal direction, or both from a relaxed state to an expanded state by introducing the actuating fluid into the compartment of the inner member to compress the granular medium against the outer member to increase the stiffness of the device.

In some embodiments, the present devices may include multiple inner members to control the length of the device and the stiffness of the device. For example, a fluid operated device of the present embodiment may comprise a first inner member made from an elastic material and defining a compartment for receiving an actuating fluid, a second inner member made from an elastic material and defining a compartment for receiving an actuating fluid, an outer member made from an inelastic material, being disposed around the first inner member and the second inner member, and a granular medium disposed between the outer member and the first inner member and second inner member. In some embodiments, the second inner member may be wrapped around the first inner member. In some embodiments, the second inner member may be spiral in shape or cylindrical shell shaped. The first inner member may be moveable in the longitudinal direction from a relaxed state to an expanded state by introducing the actuating fluid into the compartment of the first inner member to increase the length of the device. The second inner member may be moveable in a radial direction from a relaxed state to an expanded state by introducing the actuating fluid into the compartment of the second spiral inner member to compress the granular medium against the outer member to increase the stiffness of the device.

Figure 1:
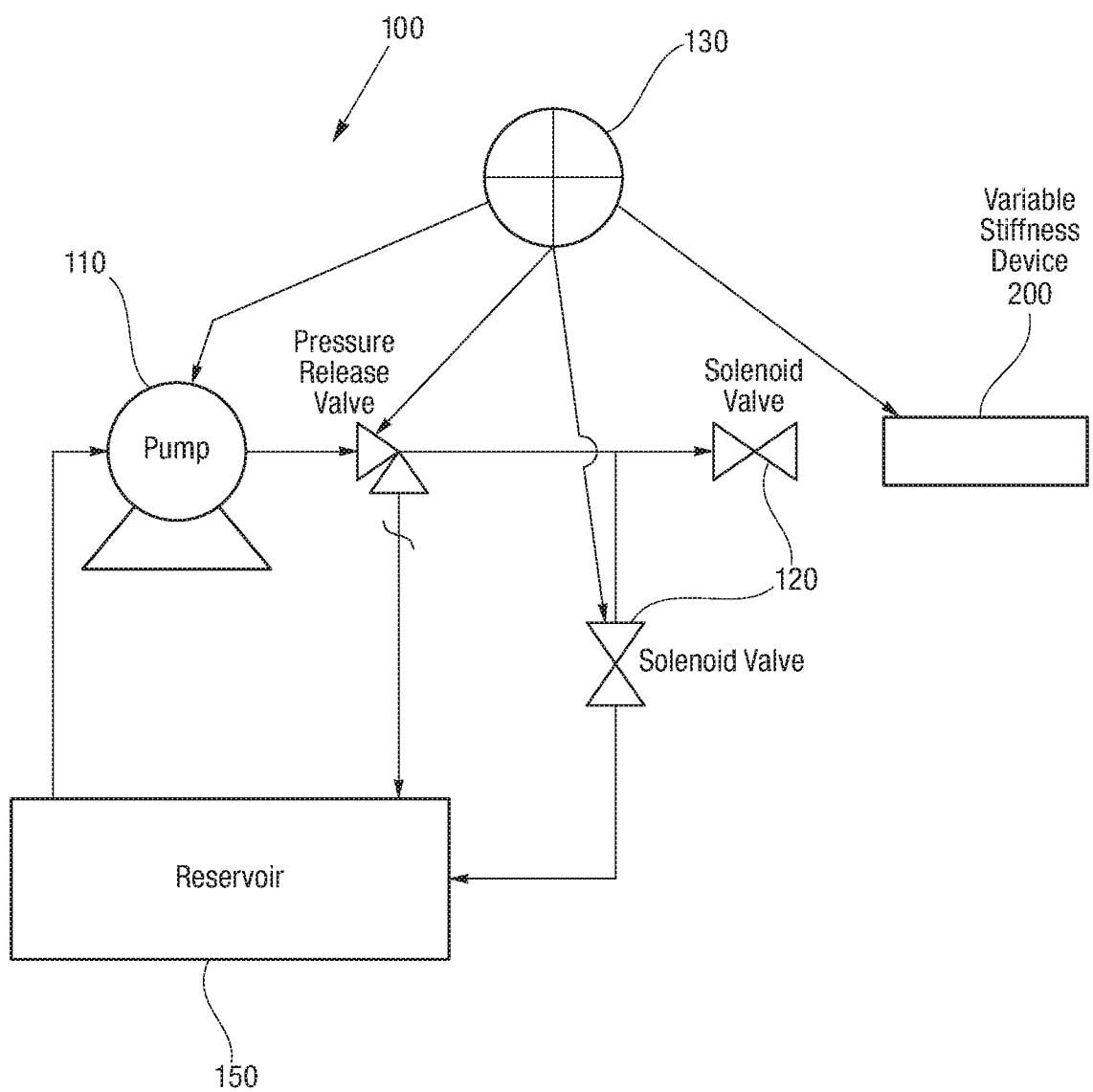
FIG. 1 illustrates a example of an actuator system and variable stiffness device according to the present disclosure.

FIG. 1 illustrates a non-limiting embodiment of a hydraulic system 100 for use with the present variable stiffness devices 200. In some embodiments, the hydraulic system 100 may include a pump 110, one or more valves 120, a controller 130 and one or more variable stiffness devices 200 that can act as an artificial bone with variable stiffness. The actuator system 100 may further include a reservoir 150 for a fluid used to actuate the elastic actuator. In operation, the pump may be used to pump the actuating fluid from the reservoir into the variable stiffness devices 200 to change the stiffness of the variable stiffness devices 200, as is described in more detail below. Once a desired pressure is achieved, the variable stiffness devices 200 may be maintained at the desired pressure and stiffness to support a load. When the fluid is discharged from the elastic actuator, the pressure release from the actuator causes the variable stiffness devices 200 to decrease in stiffness and become more flexible. The controller 130 is in communication with the component of the actuator system 100, as shown in FIG. 1, to control the operation of the actuator system 100. The controller can be any type of controller known and used in the art. It should be noted that other hydraulic systems can also be used. In some embodiments, a pneumatic system may be employed to operate the variable stiffness devices of the present disclosure. For example instead of a pump, reservoir, and valves, in some embodiments, direct fluid volume management may be used, such as for example, utilizing motorized lead screw in series with syringe's plunger, or a hydraulic single acting or double acting cylinder. In some embodiments, a simple user powered pump can be also utilized for manual pressurization of the present devices.

Figure 2A:
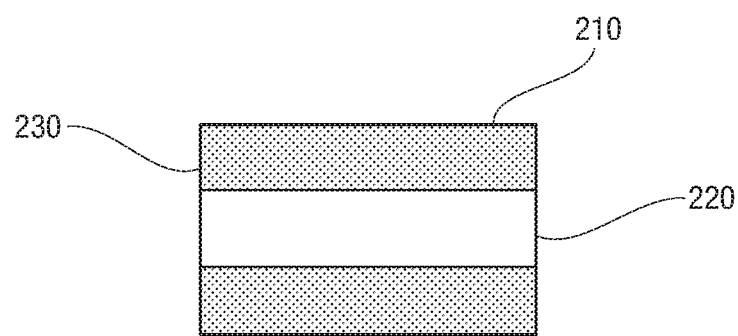
FIG. 2A and FIG. 2B illustrate a side view of one embodiment of a variable stiffness device of the present disclosure in a relaxed state (FIG. 2A) and stiffened state (FIG. 2B).
Figure 2B:
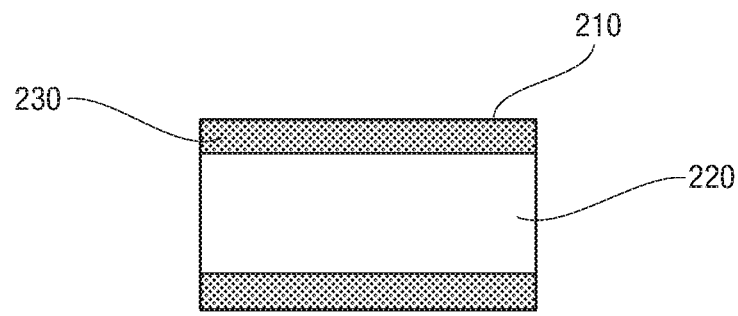
Figure 2C:
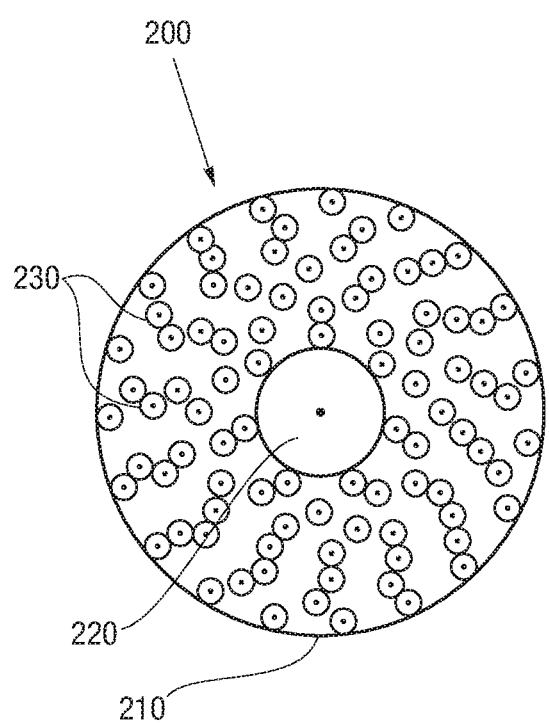
FIG. 2C and FIG. 2D illustrate a cross-sectional view of one embodiment of a variable stiffness device of the present disclosure in a relaxed state (FIG. 2C) and stiffened state (FIG. 2D).
Figure 2D:
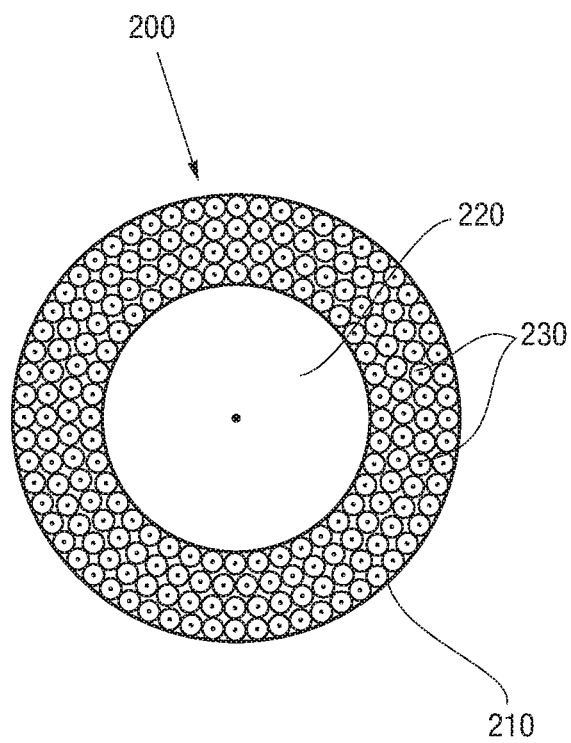

In reference to FIGS. 2A-2D, in some embodiments, the variable stiffness device 200 includes an inner member 220 surrounded by an outer member 210 with a layer of granular medium 230 disposed between the inner member 220 and the outer member 210. In some embodiments, the inner member 220 forms an elongated, expandable compartment for receiving an actuating fluid. The inner member 220 can thus be moved from a relaxed state, as shown in FIG. 2A and FIG. 2C, to an expanded or pressurized state, as shown in FIG. 2B and FIG. 2D, by introducing the actuating fluid into the inner member 220 and back to the relaxed state upon discharge of the actuating fluid from the inner member 220. Pressurizing the inner member 220 may expand the inner member 220 in the radial direction, longitudinal direction or both. As the inner member expands, it may compress the granular medium against the outer member to change the stiffness of the variable stiffness device 200. When the inner member 220 is not pressurized or pressurized at small fluid pressure, the inter granular distance is large enough that granules can easily pass next to each other such that the structure is easily bendable and characterized with small stiffness. On the other hand, at higher pressures, the inter granular distance is small, i.e. granular media is jammed such that structure is rigid and characterized with large stiffness.

The inner member 220 may be made of expandable materials, preferably having one or more of the following characteristics: resistance to wear and tear, high tensile strength, resilience, and elongation. The outer member 210 may form an outer sleeve around the inner member 220 to direct or control the expansion and contraction of the inner member 220. The outer member 210 may be made of a variety of different materials, preferably having one or more of the following characteristics: cloth like inelastic, tough, with low absorption of moisture and a high flexural strength, in radial direction, linear direction or both. In some embodiments, the outer member may be made of polyester. In some embodiments, the outer member 210 may be rigid or non-stretchable in the radial or outward direction but compressible in the axial or longitudinal direction. In some embodiments, the outer member may be corrugated or may utilize a telescoping mechanism, for example, with concentric cylinders. In some embodiments, the outer member 210 has a fixed size in the radial direction and a variable size in a longitudinal direction. In some embodiments, the outer member 210 may contract by wrinkling or bending under compressive load.

The variable stiffness devices 200 may linearly or axially contract under compressive load and exhibit variable stiffness behavior, which directly correlates to amount of fluid pressure applied within the inner member 220. During contraction the outer member may wrinkle. If compressive load is too large for given pressure the device 200 may buckle to one side. In some embodiments, one side of variable stiffness device outer member 210 can be reinforced, in part or in whole. In some embodiments, the reinforcement may be used to direct bending in a desired direction. In some embodiments, the variable stiffness devices 200 of the present disclosure can be slightly pre-bent even without compressive load such that variable stiffness device naturally bends, i.e. buckles, to a desired side. In some embodiments, one side of the variable stiffness device outer member 210 can be reinforced with rigid element to prevent buckling.

Figure 3A:
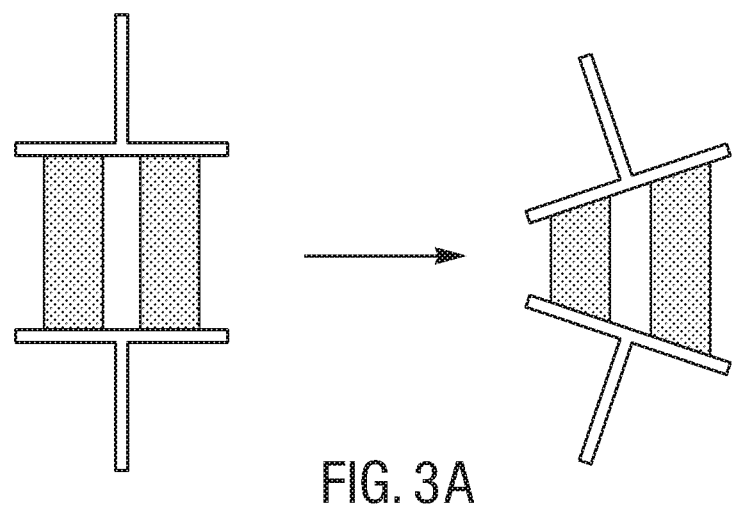
FIGS. 3A-3B illustrate an embodiment of a rotary joint employing variable stiffness devices of the present disclosure.
Figure 3B:
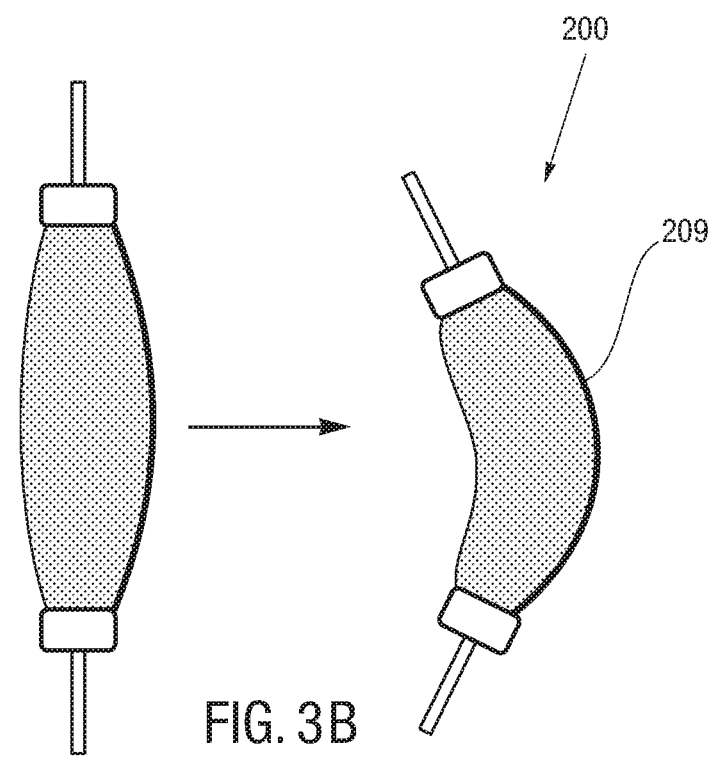

The buckling for typical support element applications is considered undesirable. However, for applications where variable stiffness device is considered part of the rotary joint the controlled buckling may be considered desirable. In some embodiments, the variable stiffness devices 200 may be utilized as part of a rotary joint, and one or more of variable stiffness devices 200 with and without buckling may be utilized to generate variable stiffness rotary dynamics under compressive load. FIG. 3A illustrates an embodiment of a rotary joint with multiple variable stiffness devices 200, without buckling. FIG. 3B illustrates an embodiment of a rotary joint with a variable stiffness device with a single variable stiffness device 200, with a reinforcement 209 on one side to induce controlled buckling or bending to a desired side.

In some embodiments, the inner member 220 is comprised of an elastic material allowing for expansion of the inner member 220 in the radial direction. In some embodiments, the inner member 220 may be formed from latex material, and the outer member may be made from polyester or nylon. The outer member 210 is comprised of an inelastic material which is configured to limit expansion of the inner member 220 in the radial direction. The outer member 210 is made of an inelastic material to allow the compression of the granular medium 230 against it and to limit the diameter of the device. When the actuator fluid is delivered to the inner member 220, the inner member expands and the granular medium 230 are compacted and compressed between the inner member 220 and the outer member 210, in a manner known as granular jamming. This allows the granular medium 230 to move past each other and leave a flexible device 200 when unpressurized, but creating a much stiffer device 200 with a higher compressive strength when the device 200 is pressurized.

The outer member 210 may be designed to prevent or at least minimize radial expansion of the inner member 220. To that end, it is desirable that when the outer member 210 is expanded there are no openings in the outer member 210 through which the granular medium 230 or any portion of the inner member 220 can protrude in radial direction when pressurized. In some embodiments, the outer member 210 can be made from a sheet of material which in the expanded state has no openings to provide an unbroken or uninterrupted barrier which prevents the granular medium 230 or the inner member 220 from protruding through the outer member 210, in whole or in part. By way of a non-limiting example, the outer member 210 may be made from a corrugated fabric or cloth like material. The expansion of such outer member is not likely to create any openings in the outer member through which the granular medium 230 or the pressurized inner member 220 may protrude, in whole or in part. In some embodiments, the outer member 210 is allowed to expand in longitudinal direction, if necessary, by unfolding the folds of the outer member 210, rather than by simply stretching the outer member 210, which may result in unwanted openings.

In some embodiments, the granular medium 230 may be compressible, such as rubber, such that the device 200 will get stiffer as the pressure of the actuator fluid delivered to the inner member 220 is increased. In some embodiments, the granular medium may include granulated EPDM (ethylene propylene diene monomer) rubber for the granular media due to the inexpensive cost, ease of sourcing, and lack of reactions with water. In some embodiments, other granular medium can be used depending on the desired strength or stiffness of the variable stiffness devices, type of materials, average particle size, particle geometry, and the packing factor of the granular medium.

In some embodiments, elastic, ethylene propylene diene monomer (M-class) rubber (EPDM) granule may be utilized. In some embodiments, rigid silicon sand granules can be used. In some embodiments, the elastic granular medium can be a mixture of rubber pellet granules ranging from about 1 to about 3 mm in diameter. For granules not being perfectly spherical in shape, the granular medium can exhibited similar properties in terms of packing factor ranging in between 0.55 and 0.74 in unpressurized state (i.e. at atmospheric pressure) depending on applied packing as observed for granular medium with spheres. Upon pressurization the packing factors can reach close to 0.95 packing factor due to compressible nature of rubber particles.

Figures 4A, 4B, 4C:
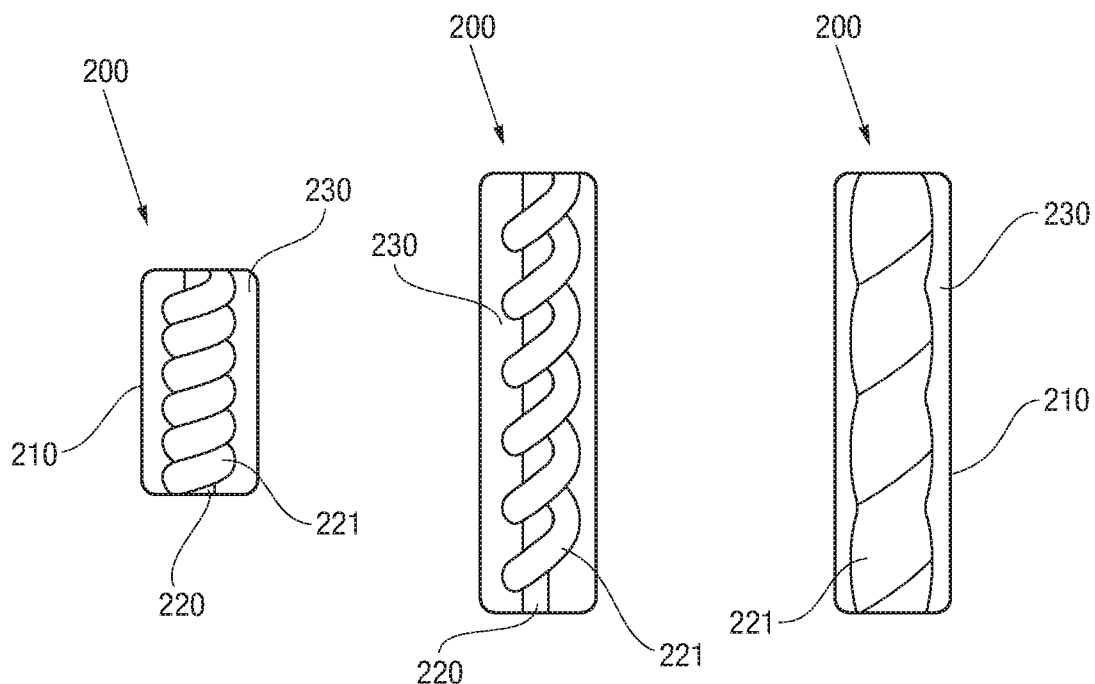
FIGS. 4A-4C illustrate another embodiment of a variable stiffness device having multiple inner members.

In reference to FIGS. 4A-4C, in some embodiments, the device 200 may comprise multiple inner members to control the length and stiffness of the device. FIG. 4A illustrates a cross section of the device in a relaxed state when neither inner member is filled with actuating fluid. FIG. 4B illustrates a cross section of the device in a lengthened state when the first inner member 220 is filled with actuating fluid to change the length of the device. FIG. 4C illustrates a cross section of the device in a lengthened and a stiffened state when the first inner member and the second inner member 221 are filled with actuating fluid. For example, the device may include an outer member 210 and a first inner member 220, a second inner member 221, and granular medium 230 placed in a layer between the outer member 210 and both the first inner member 220 and second inner member 221.

The first inner member 220 may control longitudinal, i.e. axial, i.e. linear length and the second inner member 221 may provide variable stiffness. The granular medium 230 may be selected such particles are not allowed to pass each other when the second inner member 221 is pressurized. The first inner member 220 may be comprised of an elastic material and be primarily configured to allow for expansion of the device in the longitudinal direction. The second inner member 221 may also comprise of an elastic material but be primarily configured to allow for expansion in the radial direction. In some embodiments, the second inner member 221 is spiral in shape and wrapped around the first inner member 220. In some embodiments, the second inner member 221 is disposed coaxially with the first inner member 220. The outer member 210 is comprised of an inelastic, non-stretchable material which is configured to limit expansion of the device 200 in the radial direction.

When the actuator fluid is delivered to the first inner member 220, as demonstrated in FIG. 4B, the first inner member may expand the device 200 in the longitudinal direction. When a desired length is achieved, the second inner member 221 may be pressurized, as demonstrated in FIG. 4C, to expand the second inner member 221 in the radial direction. This may cause the granular medium 230 to become compacted and compressed between the first inner member 220, the second inner member 221, and the outer member 210, which changes the stiffness of the device. This allows the granular medium 230 to move past each other and leave (they don't leave, they are just moving easily past each other!) a flexible device 200 (maybe have "and device 200 is soft and bendable" instead of "leave a flexible device 200") when unpressurized, but creating a much stiffer device 200 with a higher compressive strength when the device 200 is pressurized. In some embodiments, the inner members may be concentric with each other.

Figure 5:
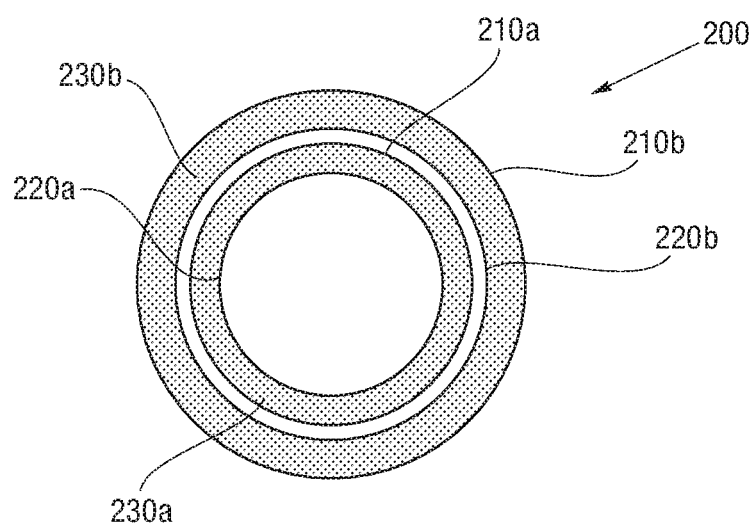
FIG. 5 illustrates another embodiment of a variable stiffness device of the present disclosure.

In reference to FIG. 5, one or more variable stiffness devices of the present disclosure may be combined. In some embodiments, a variable stiffness device 200 includes two independent variable stiffness devices, comprising an outer member 210a, 210b and an inner member 220a, 220b and granular medium 230a, 230b disposed between the outer member and the inner member. In some embodiments, the multiple variable stiffness devices are disclosed concentrically with one another, as shown in FIG. 5, but they can also be disposed in different configuration.

In some embodiments, the variable stiffness devices of the present disclosure may be used to provide structural support to a structure. The variable stiffness devices of the present disclosure may be disposed in connection with such structure and adjusted to a desired stiffness to provide a level of structural support required or desired for the structure. In some embodiments, the present variable stiffness devices may be incorporated into the structure in need of support. In some embodiments, the present variable stiffness devices may be disposed around the structure or otherwise in connection with the structure. In some embodiments, the devices of the present disclosure may be incorporated into articles of wearable clothing, braces, prosthetic sockets or fittings, walkers, crutches or exoskeletons, so the devices can help support one or more joints or other body parts of the user.

The devices of the present disclosure can be produced very inexpensively and can have a variety of applications from wearable medical devices to stand-alone robotics systems. The devices of the present disclosure can be used in a different industries and technologies, such as, for example, the health industry, medical device technologies for humans and animals, aerospace and automotive technologies, space technologies, underwater technologies, robotic system technologies and similar industries and technologies, as well as for use in exoskeletons, prosthetics and orthotics, furniture, construction, underwater, aero, space and civil engineering. In some embodiments, the devices of the present disclosure may be incorporated into an article of robotic system wherein the device is configured to help support one or more joints or other body parts of a robot. In some embodiments, the devices of the present disclosure may be incorporated into an article of active suspension and impact management for automotive system, wherein the device is configured to help support and manage forces onto one or more elements of automotive system. In some embodiments, the devices of the present disclosure may be incorporated into an article of structural support for furniture (chairs, beds etc) and tent elements, wherein the present device can be configured to help support and manage forces applied onto these structure and/or user.

Figure 6:
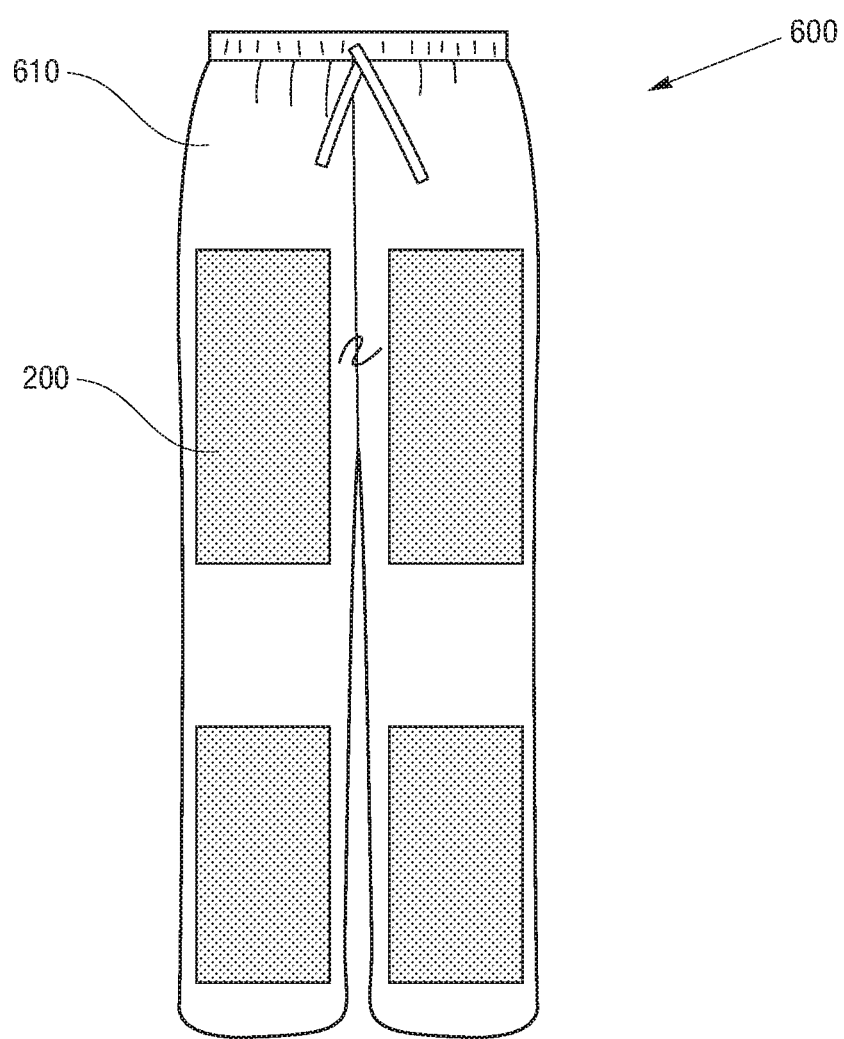
FIG. 6 illustrates an embodiment of an article of clothing employing variable stiffness devices of the present disclosure.

In reference to FIG. 6A, in some embodiments, one or more variable stiffness devices 200 of the present disclosure may be combined with a wearable article of clothing 610, to form an exoskeleton. When the user wears the article of clothing 610, the one or more variable stiffness devices 200 can be positioned substantially along the clothing to best provide support to the user in the manner of representing an artificial bone. For example, the devices may help support or protect user's joints when carrying a load. In some embodiments, the device may be shaped to conform to the shape of the user's limbs for additional comfort. In some embodiments, multiple devices may be incorporated into a wearable clothing 610 to help protect multiple joints of the user. In some embodiments, the device when combined with a wearable article of clothing 610 is configured to have a light support structure, i.e. variable shape and stiffness, utilizing the stiff, variable stiffness device, which can be tuned "on the fly" to transition from being a very stiff, rigid support to a completely soft, bendable material. The size and shape can also be also tuned during operation. The exoskeleton device may be adjustable for specific users and/or intended tasks of specific users.

It should be noted that the devices 200 of the present disclosure may also be used to assist in muscular movement of the wearer. For example, as discussed above, the inner member may be expandable in the longitudinal direction, with or without expansion in the radial direction by introducing the actuating fluid therein and may be allowed to contract in upon discharge of the actuating fluid. In this manner, the contracting movement of the inner member can be used as the muscle force, creating a tensile force similarly to an actual biological muscle to, for example bend the limbs of the joint. Additionally or alternatively, the variable stiffness devices of the present disclosure may be combined in the exoskeleton with variable stiffness devices that mimic muscle movement, such as for example, disclosed in U.S. application Ser. No. 14/628,663, which is incorporated herein by reference in its entirety.

In some embodiments, the variable stiffness devices may be controlled using an automatic controller. The experimentally established relationship between fluid pressure and critical buckling force, i.e. minimal compressive force that could cause device to buckle, can be utilized for automatic control of stiffening or softening of the present variable stiffness devices based on applied compressive force. The automatic control can be used to prevent buckling of the variable stiffness devices under compressive load and also to soften device as much as necessary. For applied compressive forces that are larger than demarcation force, defined as, for example, 25N below critical buckling force for given fluid pressure, the system can be configured to increase the fluid pressure and hence increase the critical buckling force such that force difference in between critical force and measured force is larger than 25N. Similarly if the measured compressive force is substantially smaller than demarcation force, the system can be configured to lower fluid pressure, hence lowering the buckling force, and therefore lowering the demarcation force. Other control methodologies may be used to control stiffness by varying pressure in relation to critical buckling force as well as in relation to other desired metrics (e.g. user comfort).

Examples, which are set forth to aid in the understanding of the disclosure, and should not be construed to limit in any way the scope of the disclosure as defined in the claims which follow thereafter. The following examples are put forth so as to provide those of ordinary skill in the art with a complete disclosure and description of how to make and use the embodiments of the present disclosure, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for.

EXAMPLES

Example 1

Devices were constructed using granulated EPDM (ethylene propylene diene monomer) rubber for the granular media. The potential for use of other granulation is possible, with the likelihood that the device's strength would change according to certain properties, such as the material used, average particle size, particle geometry, and the packing factor. Previous tests have utilized coffee, salt, and hydrophobic sand as different granulations.

A test device was built, filling the excess space with the rubber pellets before being sealed at both end with a pipe clamp. The rubber tubing was connected to ½ in. NPT threaded connectors, which were then screwed into machined aluminum block end-pieces. The tubing used had inner and outer diameters of ½ and ⅞ inches, respectively. The final outer diameter was approximately 1.5 inches.

A secondary hole was placed in the base of one block to serve as the input for water to pressurize the device, and was sealed off during testing. Testing was completed at the three following pressures, 0 (no water), 70, and 110 PSI. Pressures were confirmed with a gauge prior to testing, but were not rechecked during or after testing was complete.

For the testing, an Instron 5567A machine running the Blue Hill 2 Software with flat compressive grips was used to place a load on the sample. The crosshead speed compressed at a rate of 0.2 in/min, and was manually stopped after it was felt that the critical data was collected, usually around one inch of compression. Collected data included time, position, and force in pounds. The results can be seen in FIG. 7.

Figure 7:
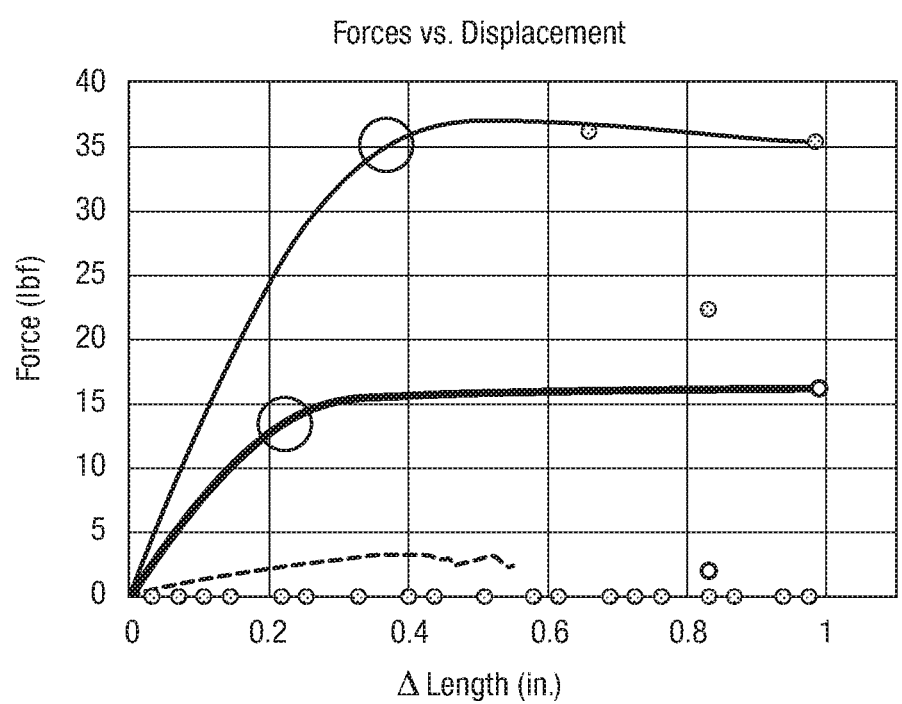
FIG. 7 is a force as a function of displacement graph comparing points of failure (structure starts to bend) of variable stiffness devices at varying fill pressures.

Points circled in black on FIG. 7 are considered approximate points of failure, as the testing setup was not capable of identifying a single point in time that served as failure. Failure was classified as buckling of the device, with there being bending in the center, and a noticeably reduced increase in the compressive force for an equal amount of displacement. Peak forces for the three curves were about 5, 17, and 35 lb for the pressures of 0, 70, and 110 PSI, respectively.

Testing results show that device stiffness increases in correlation with an increase in the internal fluid pressure. Additionally, the data suggests the higher stiffness correlates with a greater displacement needed to reach failure. The test completed at 0 PSI (no water in the device) can be considered to have failed from the start, as the device quickly buckled during compression, and offered very little resistive force, as can be seen in FIG. 4. However, for example the experimentally obtained Young's Modulus of same device increased from 0.70 MPa at 0.21 MPa fluid pressures, to 3.53 MPa at 0.55 MPa fluid pressures, which is five-fold increase in stiffness over moderate range of fluid pressure. In comparison, pressurizing the device up to 110 PSI can significantly increase the strength of the device.

Example 2

Figure 8:
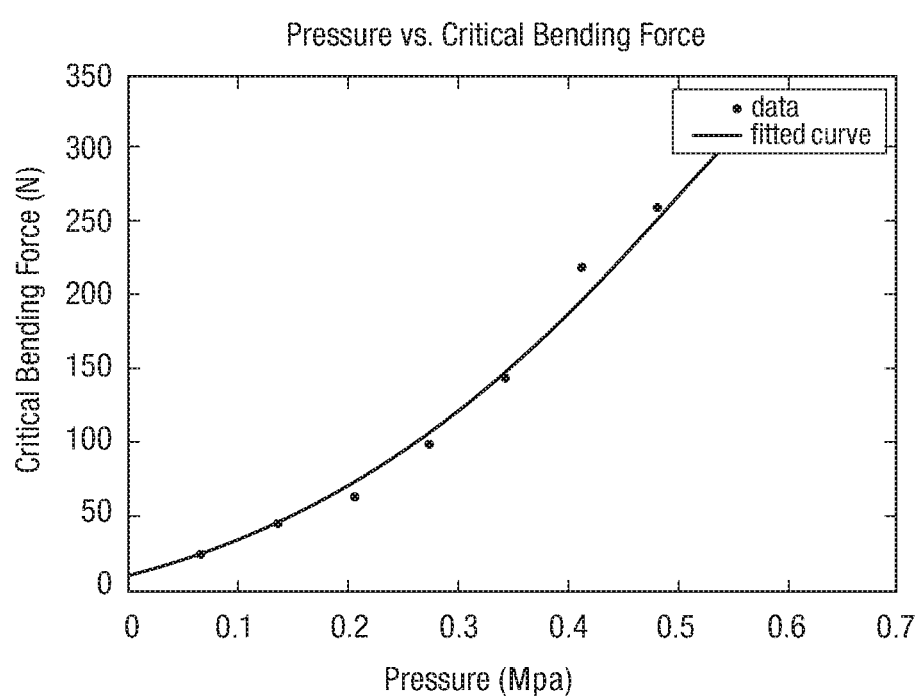
FIGS. 8-9 present modeling data for a controller configuration to control a variable stiffness device of the present disclosure.

The operation of a control system were modeled. The system included an inlet pump in series with the variable stiffness device and a branched exit controlled by a solenoid valve. A controller was designed and implemented to control the solenoid valve, based on the critical bending forces collected on the variable stiffness device. An Arduino Uno microcontroller was used in order to actuate the solenoid valve. The critical bending forces for the variable stiffness device at different pressures were plotted and a 2nd order polynomial curve fit was applied to compute the equation of critical bending force as a function of pressure (Pressure (MPa) Vs. Critical Load (N)), as shown in FIG. 8.

In the real time implementation of the controller, the pressure and load data were collected and the critical bending force for the corresponding pressure was calculated using the following equation:

$$F_C = 715.5P^2 + 155.7P + 10.44 \quad (1)$$

Figure 9:
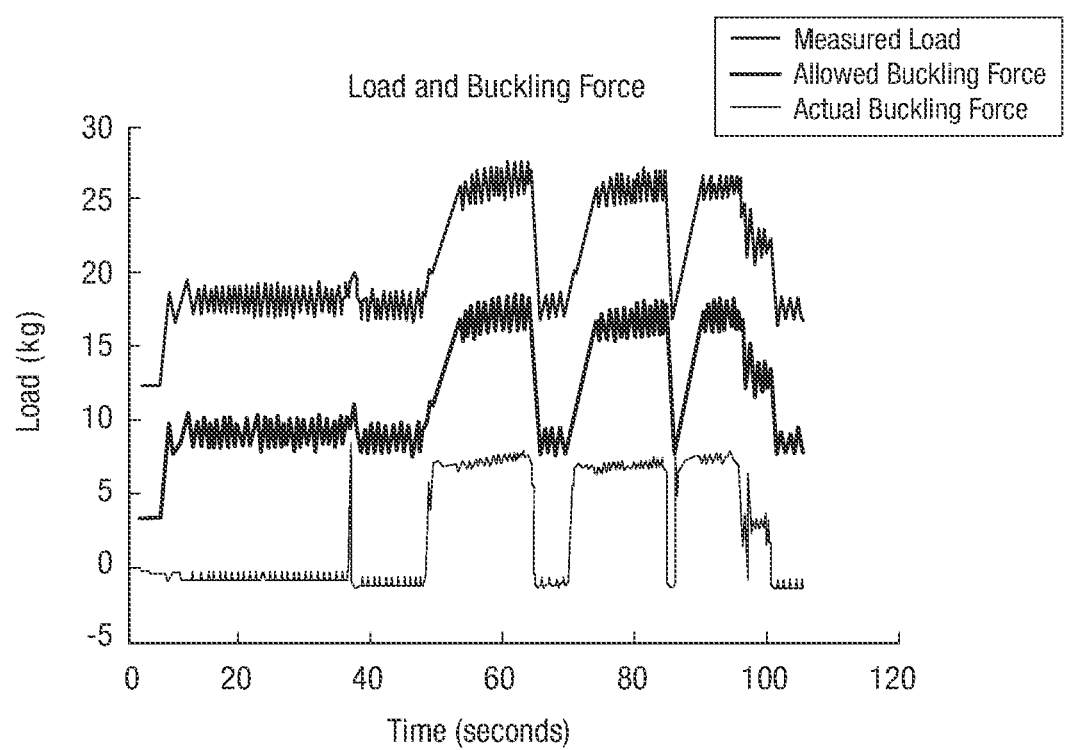

An allowed load threshold was provided such that the actual force exerted on the bone was 9.071 kg (20 lb) lower than the critical bending at all times. This ensured that the variable stiffness device was under the linear loading regime to prevent the system from buckling and subsequently cause a reduction in the critical bending force. The error between the load acting on the variable stiffness device and the allowed load was calculated and minimized for control. If the external load acting on the system changes, the new allowed load is recalculated and the exit valve is opened or closed respectively. As shown in FIG. 9, the measured load, allowed bucking and the critical buckling force over time.

To test the controller performance, a load of 9.071 kg (20 lb) was randomly applied to and removed from the load cell [18] and the system response time was determined. From FIG. 11, it can be inferred that the average response time to pressurize the bone was 3.37 seconds while the average time during depressurization was 1.19 seconds.

The entirety of the tests performed on the variable stiffness device revealed that the measured load was lower than the allowed buckling force of the system. With the system set up having a virtual load threshold of 9.071 kg added to it, the critical buckling force of the system was never reached.

TABLE 1

Mean, Standard Deviation, Minimum, and Maximum values for Error volumetric flow rates at no load.

| Volumetric Flow Rate (cm³/sec) | Error | | | |
|---|---|---|---|---|
| | Mean | Std. Deviation | Min | Max |
| 12.2 | 0.455 | 0.736 | −0.562 | 1.687 |
| 15 | 0.297 | 0.589 | −0.621 | 1.288 |
| 24.6 | 0.838 | 0.784 | −0.522 | 2.109 |
| 44.4 | 0.937 | 0.796 | −0.535 | 2.413 |
| 92.3 | 0.876 | 0.797 | −1.461 | 2.254 |

The controllability of the system was measured under various flow rates. Due to the fixed opening of the solenoid valve, the exit flow rates varied significantly even though valve was opened instantaneously. Therefore, individual no-load tests for the error were performed at varying flow rates and the mean, standard deviation, minimum, and maximum errors are listed in Table 1.

All patents, patent applications, and published references cited herein are hereby incorporated by reference in their entirety. It should be emphasized that the above-described embodiments of the present disclosure are merely possible examples of implementations, merely set forth for a clear understanding of the principles of the disclosure. Many variations and modifications may be made to the above-described embodiment(s) without departing substantially from the spirit and principles of the disclosure. It will be appreciated that several of the above-disclosed and other features and functions, or alternatives thereof, may be desirably combined into many other different systems or applications. All such modifications and variations are intended to be included herein within the scope of this disclosure, as fall within the scope of the appended claims.

What is claimed is:

1. A wearable device comprising:
an article of clothing and one or more variable stiffness devices associated with the article of clothing, wherein at least one of the one or more variable stiffness devices comprises:
an inner member moveable in a radial direction from a relaxed state to an expanded state;
an outer member disposed around the inner member, the outer member having a fixed size in the radial direction; and
a granular medium disposed between the inner member and the outer member;
wherein, as the inner member moves from the relaxed state to the expanded state, the inner member compresses the granular medium against the outer member to increase a stiffness of the variable stiffness device.

2. The wearable device of claim 1 wherein the inner member defines a compartment for receiving an actuating fluid, and is moveable from the relaxed state to the expanded state by introducing the actuating fluid into the compartment of the inner member.

3. The wearable device of claim 1 wherein the outer member has a variable size in a longitudinal direction.

4. The wearable device of claim 1 wherein the inner member is made from an elastic material and the outer member is made from a non-stretchable material.

5. The wearable device of claim 1 wherein the outer member is reinforced on a side to direct bending of the outer member under a load.

6. The wearable device of claim 1 wherein the outer member is pre-bent to a side to direct bending of the outer member under a load.

7. The wearable device of claim 1 wherein the granular medium is compressible.

8. The wearable device of claim 1 wherein the granular medium is a mixture of rubber pellet granules ranging from about 1 to about 3 mm in diameter.

9. The wearable device of claim 1 wherein the granular medium has a packing factor between about 0.55 and about 0.74 at atmospheric pressure.

10. A wearable device comprising:
an article of clothing and one or more variable stiffness devices associated with the article of clothing, wherein at least one of the one or more variable stiffness devices comprises:
a first inner member, the first inner member defining a first compartment for receiving a first actuating fluid;
a second inner member wrapped around the first inner member, the second inner member defining a second compartment for receiving a second actuating fluid;
an outer member disposed around the inner member; and
a granular medium disposed between the second inner member and the outer member;
wherein the first inner member is configured to expand in a longitudinal direction by introducing the first actuating fluid into the first compartment of the first inner member to expand the variable stiffness device in the longitudinal direction; and
wherein the second inner member is configured to expand in a radial direction by introducing the second actuating fluid into the second compartment of the second inner member to compress the granular medium against the outer member to increase a stiffness of the variable stiffness device.

11. The wearable device of claim 10 wherein the outer member has a fixed size in the radial direction and a variable size in the longitudinal direction.

12. The wearable device of claim 10 wherein the outer member is reinforced on a side to direct bending of the outer member under a load.

13. A method for providing structural support to a structure, the method comprising:
disposing a variable stiffness device in connection with a structure in need of structural support, the variable stiffness device comprising an inner member defining a compartment for receiving an actuating fluid; an outer member disposed around the inner member; and a granular medium disposed between the inner member and the outer member;
expanding the inner member by introducing an amount of the actuating fluid into the compartment of the inner member to compress the granular medium against the outer member; and
adjusting the amount of the actuating fluid in the compartment to vary an amount of structural support provided by the variable stiffness device,
wherein the outer member has a fixed size in a radial direction and a variable size in a longitudinal direction.

14. The method of claim 13 wherein the inner member is made from an elastic material and the outer member is made from a non-stretchable material.

15. The method of claim 13 wherein the outer member is reinforced on a side to direct bending of the outer member under a load.

16. The method of claim 13 wherein the outer member is pre-bent to a side to direct bending of the outer member under a load.

17. The method of claim 13 wherein the granular medium is a mixture of rubber pellet granules ranging from about 1 to about 3 mm in diameter.

18. The method of claim 13 wherein the granular medium has a packing factor between about 0.55 and about 0.74 at atmospheric pressure.

19. The method of claim 13 further comprising incorporating the variable stiffness device into an article of clothing.

* * * * *